(12) United States Patent
Tenhuisen et al.

(10) Patent No.: US 6,648,849 B2
(45) Date of Patent: Nov. 18, 2003

(54) MEDICINAL IMPLANT AND DEVICE AND METHOD FOR LOADING AND DELIVERING IMPLANTS CONTAINING DRUGS AND CELLS

(75) Inventors: Kevor S. Tenhuisen, Clinton, NJ (US); Joel Rosenblatt, Watchung, NJ (US); John McAllen, III, Point Pleasant, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/892,342

(22) Filed: Jun. 27, 2001

(65) Prior Publication Data

US 2003/0004491 A1 Jan. 2, 2003

(51) Int. Cl.$^7$ .............................................. A61M 31/00
(52) U.S. Cl. .......................... 604/60; 604/502; 604/57; 424/423
(58) Field of Search .................... 604/502, 518–520, 604/57, 59, 60–64, 82, 285–288; 606/116, 117; 424/422, 423, 408; 222/187

(56) References Cited

U.S. PATENT DOCUMENTS

| | | | |
|---|---|---|---|
| 3,324,854 A | 6/1967 | Weese | |
| 4,402,308 A | 9/1983 | Scott | |
| 4,403,987 A | 9/1983 | Gottinger | |
| 4,451,253 A | 5/1984 | Harman | |
| 4,601,699 A | 7/1986 | Crain | |
| 4,661,103 A | 4/1987 | Harman | |
| 4,687,001 A | 8/1987 | Arko | |
| 4,753,636 A | 6/1988 | Free | |
| 4,820,267 A | 4/1989 | Harman | |
| 4,834,704 A | 5/1989 | Reinicke | |
| 4,846,793 A | 7/1989 | Leonard et al. | |
| 4,871,094 A | 10/1989 | Gall et al. | |
| 4,900,304 A | 2/1990 | Fujioka et al. | |
| 4,915,686 A * | 4/1990 | Frederick ...................... | 604/60 |
| 4,941,874 A | 7/1990 | Sandow et al. | |
| 4,950,234 A | 8/1990 | Fujioka et al. | |
| 4,966,589 A | 10/1990 | Kaufman | |
| 4,994,028 A | 2/1991 | Leonard et al. | |
| 5,024,665 A | 6/1991 | Kaufman | |
| 5,279,555 A * | 1/1994 | Lifshey ...................... | 604/223 |
| 5,284,479 A * | 2/1994 | de Jong ....................... | 604/60 |
| 5,300,079 A | 4/1994 | Niezink et al. | |
| 5,304,119 A * | 4/1994 | Balaban et al. ............. | 604/107 |
| 5,395,317 A | 3/1995 | Kambin | |
| 5,570,690 A * | 11/1996 | Yoon .......................... | 600/587 |
| 5,874,098 A | 2/1999 | Stevens et al. | |
| 5,984,890 A | 11/1999 | Gast et al. | |
| 6,074,673 A | 6/2000 | Guillen | |
| 6,296,632 B1 * | 10/2001 | Luscher et al. ............. | 604/264 |
| 6,299,590 B1 * | 10/2001 | Luscher et al. ............. | 604/11 |

FOREIGN PATENT DOCUMENTS

| | | |
|---|---|---|
| EP | 0292936 | 11/1998 |
| EP | 0990450 | 4/2000 |
| WO | 8806905 | 9/1988 |
| WO | 9953991 | 10/1999 |

* cited by examiner

Primary Examiner—Brian L. Casler
Assistant Examiner—Catherine Serke

(57) ABSTRACT

A system for injecting controlled release medicinal implants has a syringe-like injector body with a lumen and plunger. A needle is attached to the injector body and receives therein an injectable implant with an internal hollow. The implant is retained in the needle by friction, which is overcome by the plunger upon dispensing. As the plunger moves from the retracted position to the deployed position, it forces a medicament previously loaded into the injector body into the implant hollow and then pushes the implant out of the needle into the creature into which the needle has been inserted. The implant may contain a filler to absorb flowable medicaments to aid in their retention within the implant. As in known implants, the medicament is released gradually depending upon the dissolution rate of the implant body which is formed from a biodegradable material. Because the medicament is loaded into the implant at the time of injection, issues concerning the reaction of the medicament with the implant material during preparation and storage are eliminated.

26 Claims, 5 Drawing Sheets

MEDICINAL IMPLANT AND DEVICE AND METHOD FOR LOADING AND DELIVERING IMPLANTS CONTAINING DRUGS AND CELLS

FIELD OF THE INVENTION

The present invention relates to a device for inserting or implanting a solid or semi-solid drug or cell delivery implant subcutaneously, interstitially or intramuscularly. More particularly, the invention relates to a device for loading a solution, suspension, a flowable phase or a solid into a delivery implant at the time of use followed by implantation of the implant under the surface of the skin or within the muscle of a human or animal.

BACKGROUND OF THE INVENTION

Implantation of medical devices is a widely accepted medical procedure to deliver medicaments, such as pharmaceutical agents and bioactive compounds, for treatment of disease in humans and other species. Many types of medicaments have been delivered as implants, including hormones for reproductive control, vaccines, and antibiotics. In more recent technologies, the implantable composition has contained the medicament in a biologically compatible adsorbing polymer matrix. However, these compositions are prepared prior to use and suffer from the inherent problems presented by processing a polymer with a medicament. These difficulties include the use of complex processing techniques to avoid degrading the active agent in the medicament and concerns about the shelf-life of the polymer/medicament composition after processing and compatibility/reactivity between the medicament and the polymer. For example, an aqueous based medicament will degrade a biodegradeable polymer implant.

While the prior art is replete with various medicament implants, e.g., in pelletized form, as well as, various apparatus for loading and introducing such implants into the body of a living creature, it does not adequately address the above stated concerns by providing a simple medicinal implant loading and injecting mechanism that maximally preserves the medicament from degradation during the processing/formation of the implant, (which may, e.g., involve high temperatures, such as during injection molding, exposure to radiation during curing and/or sterilization) nor from degradation due to chemical reaction with the material of the implant during processing and/or storage prior to use.

SUMMARY OF THE INVENTION

The problems and disadvantages associated with the conventional techniques and devices utilized to prepare and inject medicinal implants are overcome by the present invention which includes a system for implanting medicinal implants into the body of a living creature. The system has an injector body with a first lumen therein and a plunger slideable within the first lumen between a retracted position and a deployed position. A needle having a second lumen therein is coupled to the injector body with the second lumen communicating with the first lumen. An injectable implant having an internal hollow is positionable within at least one of the first and second lumens with the hollow communicating with the first lumen. A medicament is at least partially storable within the first lumen when the plunger is in the retracted position. The internal hollow of the injectable implant receives at least a portion of the medicament when the plunger is moved from the retracted position to the deployed position. The plunger pushes the injectable implant through the second lumen and out of the needle when the plunger assumes the deployed position.

DETAILED DESCRIPTION OF THE INVENTION

The present invention provides an insertion device that loads a precise and accurate amount of an active agent into a hollow delivery implant at the time of subcutaneous or intramuscular insertion. By loading the delivery implant at the time of insertion, reaction between the medicament and the implant during implant manufacture and storage is avoided.

Figure 1:
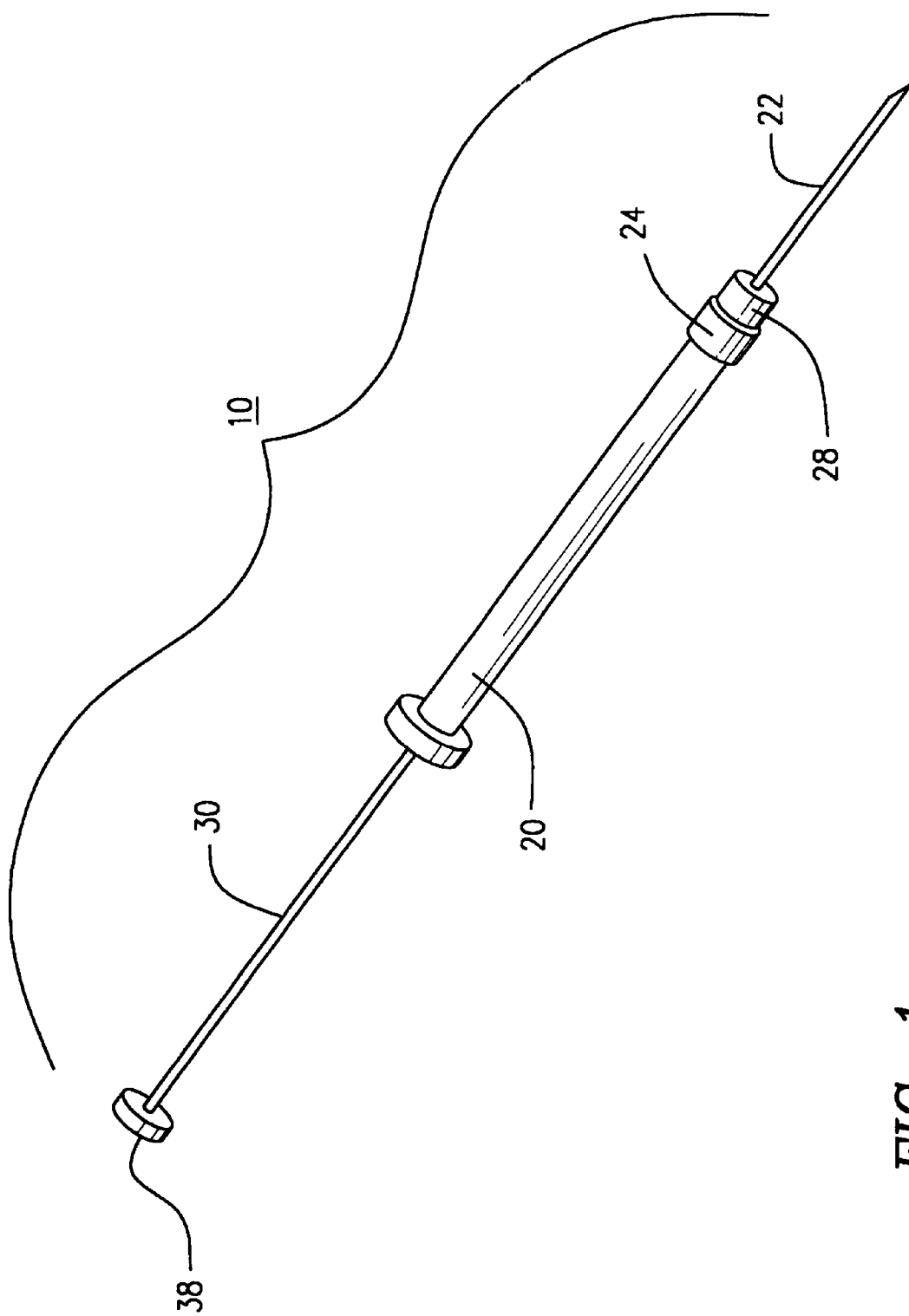
FIG. 1 is a perspective view of a device for introducing medicinal implants into the body of a human or an animal in accordance with an exemplary embodiment of the current invention.

An embodiment of the present invention is shown in FIGS. 1 to 5. FIG. 1 is a perspective view of an implant insertion device 10, having barrel 20, needle 22, and plunger 30. Both barrel 20 and needle 22 are cannulated to allow passage of plunger 30 coaxially therethrough. On the distal, or front, end of barrel 20 is hub 24 and cap 28. Both hub 24 and cap 28 have bores therein to allow passage of needle 22 and plunger 30 therethrough.

Hub 24 may be attached to barrel 20 by one of several common means. For example, hub 24 may have a female thread on the interior surface of its proximal, or rear, end that is matched to a male thread on the exterior distal surface of barrel 20. Hub 24 may also be glued (epoxied) or press fit onto barrel 20.

Cap 28 is attached to the distal end of hub 24. Cap 28 may be attached to hub 24 by one of several common means. For example, cap 28 may have a female thread on the interior surface of its proximal end, which is matched to a male thread on the exterior distal surface of hub 24.

In the alternative, the needle 22 can be attached to the barrel 20 via a Luer-type fitting, a fitting which is well known in the art. (LUER-LOK) is a registered trademark of Becton, Dickinson and Company, of Franklin Lakes, N.J. More specifically, one of the mating ends of the Luer-type fitting can be machined, molded or epoxied onto the proximal end of needle 22. The mating Leur-type fitting can be machined, molded or epoxied onto the end of the barrel 20, replacing hub 24. As yet another alternative, the entire barrel 20 and hub 24 can be molded as one piece, eliminating the need for attachment of a separate hub.

Plunger 30 extends from the proximal end of barrel 20 and partially through the cannulation (lumen) 21 (See FIG. 4) of barrel 20. Plunger 30 is provided at its proximal end with flange 38 to receive manual pressure. Flange 38 may be attached to plunger 30 by one of several common means. For example, flange 38 may have a blind hole with a female thread that is matched to a male thread on the proximal end of plunger 30. Flange 38 may also be press fit, soldered, or epoxied onto plunger 30. The plunger tip 23 (See FIG. 4) may have a plastic piston on it to better seal against the cannulation 21 of barrel 20. In addition, the distal end of plunger 30 may be beveled or rounded to ensure a smooth transition from the cannulation 21 of barrel 20 to the cannulation (lumen) 25 (See FIG. 4) of needle 22.

Suitable materials from which the barrel 20, needle 22, hub 24, cap 28, plunger 30, and flange 38 members may be formed include glasses, noncorrodible metals, noncorrodible synthetic resins such as plastics, and the like. These materials may be used alone or in combination. If the members are of glasses, noncorrodible metals, or sterilizable noncorrodible synthetic resins, they may be used repeatedly by performing sterilization. Preferably, barrel 20 is formed from glass or plastic, needle 22 and plunger 30 are formed from noncorrodible metals, and hub 24, cap 28, and flange 38 members are formed from plastic or metals.

Figure 2:
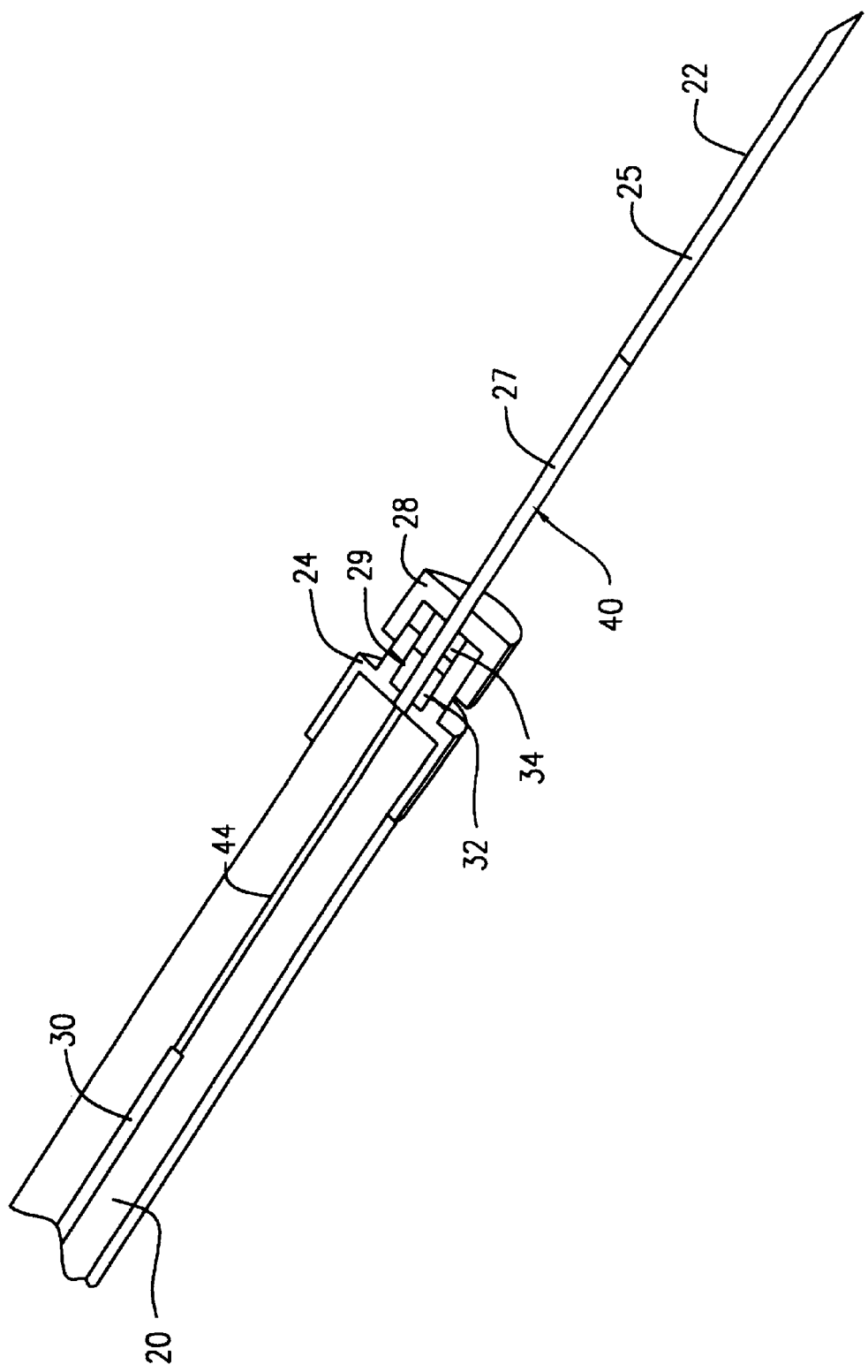
FIG. 2 is a cross-sectional view of a portion of the device of FIG. 1 prior to loading an active agent into a delivery implant held in a needle portion thereof.

FIGS. 2–5 are cross-sectional views of the distal portion of implant insertion device 10. FIG. 2 shows the distal portion of plunger 30 located in the cannulation 21 (See FIG. 4) of barrel 20. In the distal portion of the cannulation 21 of barrel 20 is located the active agent 44 to be loaded into hollow delivery implant 40 by the means discussed herein. The cross-sectional dimensions, e.g., the diameter, of the cannulation 21 of barrel 20 is matched to that of plunger 30 so that the plunger 30 may push the active agent 44 through the cannulation 21 of barrel 20 without the active agent 44 leaking between the plunger 30 and the barrel 20. This is particularly applicable to active agents 44 in liquid, gel or paste forms. The cross-sectional shape of the plunger 30 and cannulation 21 of barrel 20 may be hexagonal, octagonal, eliptical or any other shape, with a circular cross-sectional shape being preferred.

Needle 22 is located at the distal end of barrel 20, and passes through both hub 24 and cap 28. Delivery implant 40 is located in the proximal portion of the cannulation 25 of needle 20. The diameter of the cannulation 25 of needle 22 is matched to that of plunger 30 such that the plunger 30 may push the active agent 44 through the cannulation 25 without the active agent 44 leaking between the plunger 30 and the needle 22. The outer diameter of delivery implant 40 is matched to the diameter of the cannulation 25 of needle 22 to form a friction fit such that delivery implant 40 does not inadvertently slide out of the cannulation 25 of needle 22 prior to being purposely forced out by plunger 30 and to insure that the active agent does not leak between delivery implant 40 and the cannulation 25. The delivery implant 40 has a hollow bore 27 with an inner diameter that is sufficiently less than the diameter of the plunger 30, such that the plunger 30 bears upon the delivery implant 40 and does not enter the hollow bore 27 of the delivery implant 40 while the implant 40 is being forced out of the cannulation 25 of needle 22.

Collar 34 and gasket 32 are located on the proximal end of needle 22. Both are cannulated to allow coaxial placement over the needle 22. The collar 34 is press fit over the outer diameter of needle 22. The outer diameter of needle 22 is also closely matched to the diameter of the cannulation of gasket 32 such that the gasket 32 presses forcefully against the needle 22 to establish a seal, as well as to strengthen the mechanical retention of the needle 22 when the cap 28 is tightened on to the hub 24.

Suitable materials from which the collar 34 may be formed include glasses, noncorrodible metals, noncorrodible synthetic resins such as plastics, soft metal, and the like. These materials may be used alone or in combination. If collar 34 is of glass, noncorrodible metal, or sterilizable noncorrodible synthetic resin, it may be used repeatedly by performing sterilization. The collar 34 may also be disposed of as expendable after one use.

Suitable materials from which the gasket 32 may be formed include those such as, for example, noncorrodible synthetic resins such as plastics, and the like. Synthetic resins are used because gasket 32 needs to deform when attaching needle 22 to barrel 20. If gasket 32 is of sterilizable noncorrodible synthetic resin, it may be used repeatedly by performing sterilization. The gasket 32 may also be disposed of as expendable after one use.

Preferably, collar 34 is formed from noncorrodible metal, such as 304 or 316 stainless steel, and gasket 32 is formed from a noncorrodible synthetic resin such as poly(tetrafluoro ethylene), sold under the tradename TEFLON by E.I. duPont (Wilmington, Del.).

To attach needle 22 to barrel 20, the proximal end of the needle 22, gasket 32, and collar 34 assembly is first placed in the hub cannula 29. Next, the distal end of needle 22 is passed through the through hole of cap 28 until cap 28 comes into contact with the distal end of collar 34. Then, cap 28 is attached to the distal end of hub 24 by means such as those discussed above.

Figure 3:
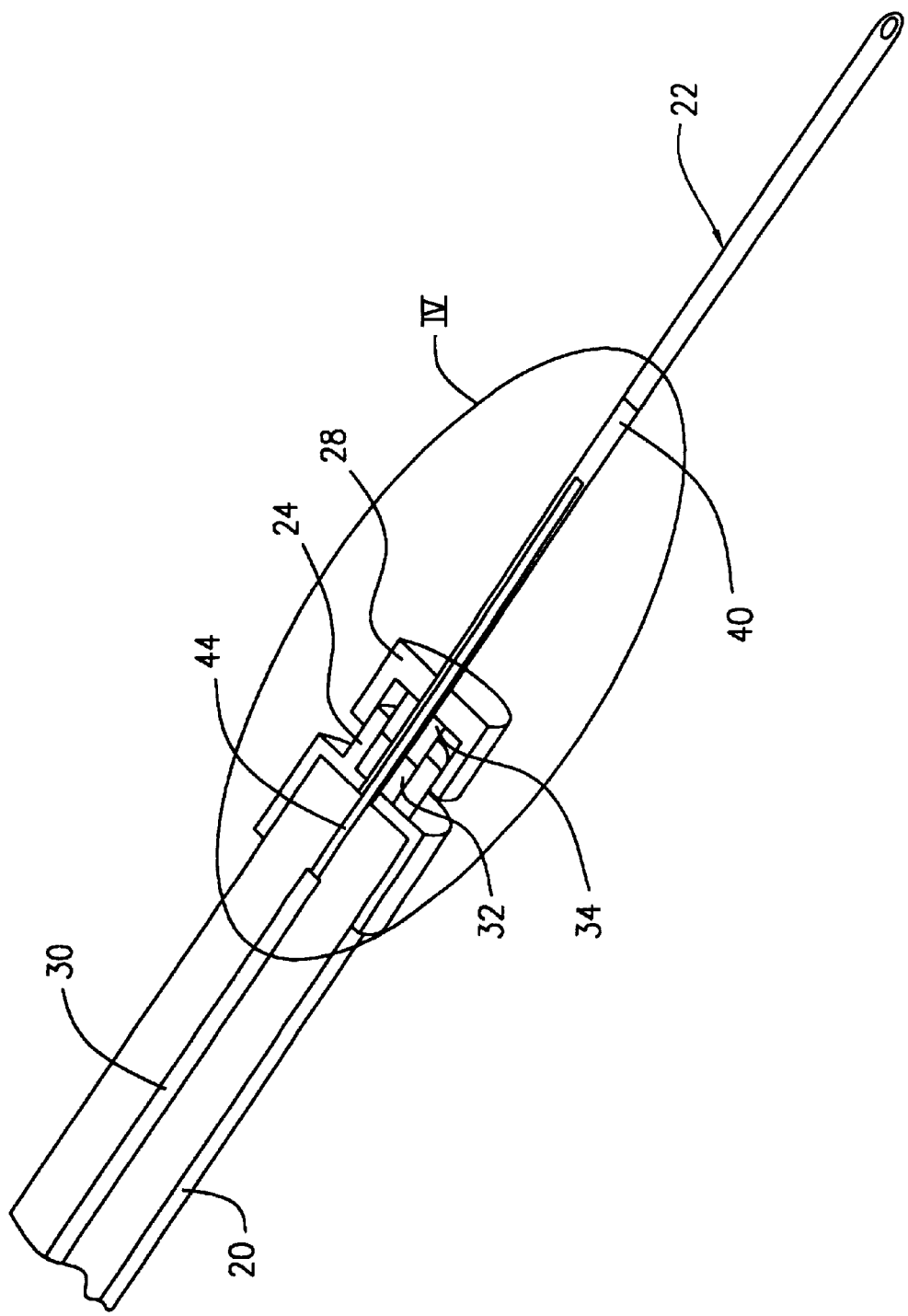
FIG. 3 is a cross-sectional view of the device of FIGS. 1 at an intermediate stage during the loading of active agent into the delivery implant.
Figure 4:
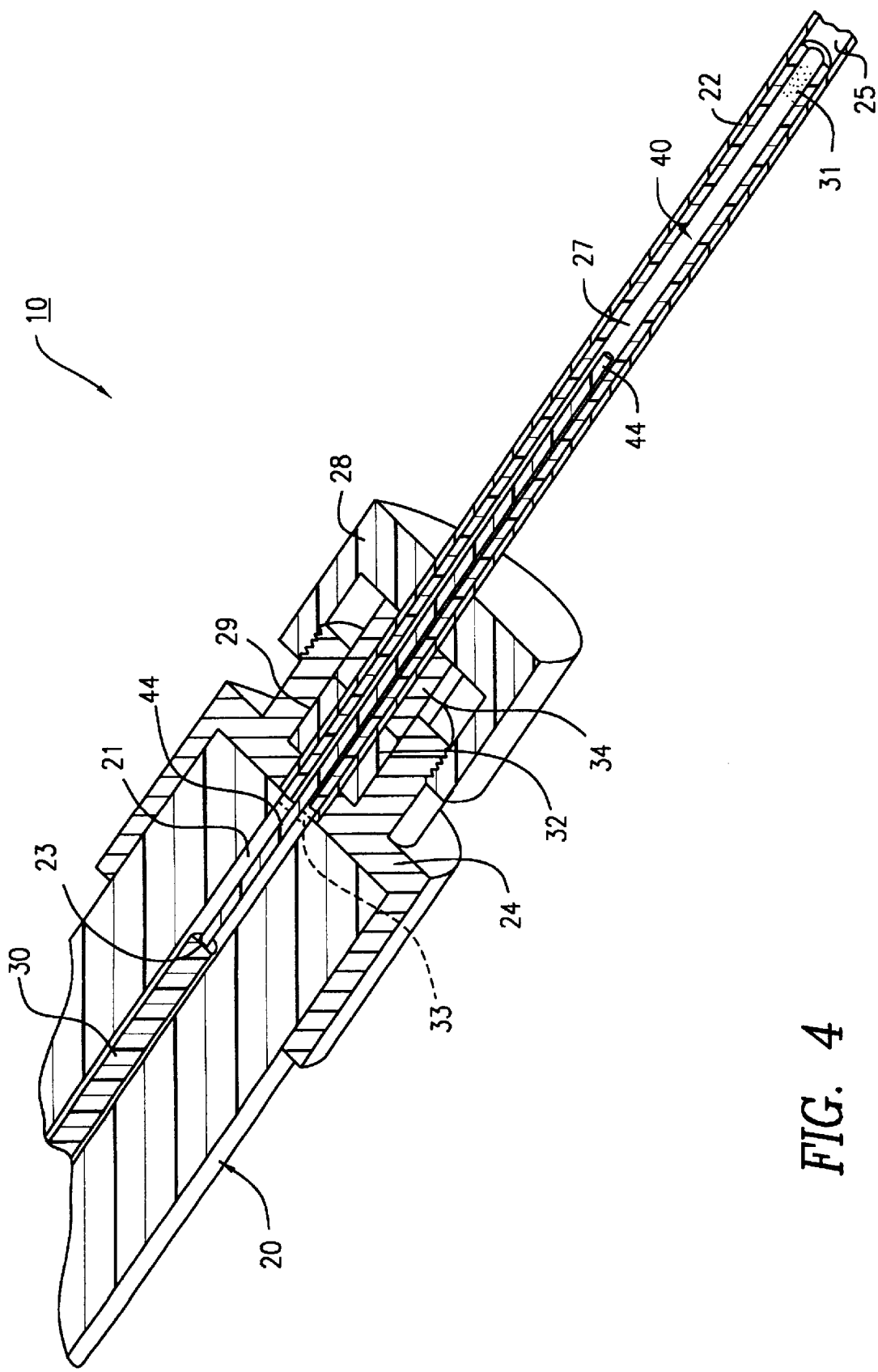
FIG. 4 is an enlarged view of a segment of the device shown in FIG. 3.

FIGS. 3 and 4 show the loading of active agent 44 into delivery implant 40. Plunger 30 is urged through the cannulation 21 of barrel 20 by application of a force on flange 38 (See FIG. 1). Active agent 44 is driven into the proximal end of delivery implant 40 hollow 27 by plunger 30. Delivery implant 40 in this embodiment is a tubular structure that is open at both distal (input) and proximal (vent) ends. This configuration permits active agent 44 to pass from the cannulation 21 of barrel 20 into the hollow 27 of delivery implant 40. Any gas trapped within the hollow 27 may be vented from the proximal end. The active agent 44 may be of a variety of compositions and may be a solid, liquid, gel, paste, suspension or combination of the foregoing. In FIGS. 1–5, the active agent 44 is depicted in the form of a solid, slender rod. A solid active agent 44 was selected to facilitate the illustration of the invention, but as noted, the active agent 44 can exhibit any selected phase. The volume of active agent 44 in the cannulation 21 of barrel 20 may be more than, less than, or equal to the volume of the hollow 27 of the delivery implant 40. Preferably, the volume of active agent 44 in the cannulation 21 of barrel 20 is matched to the volume of the hollow 27 so that active agent 44 fills the hollow 27 when the distal end of plunger 30 reaches the distal end of the cannulation 21 of barrel 20.

Figure 5:
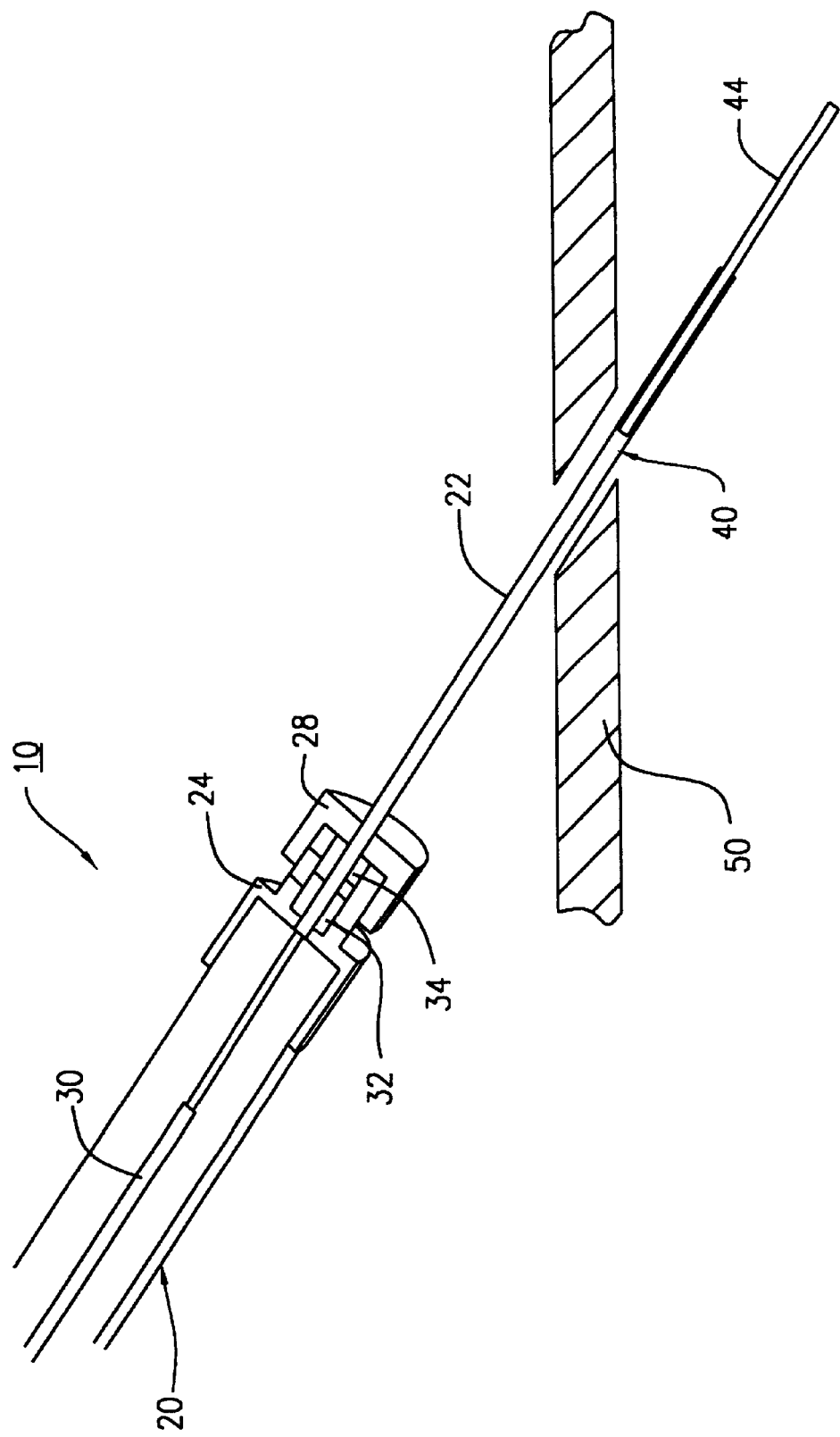
FIG. 5 is a cross-sectional schematic view of the device of FIGS. 1–4 as the delivery implant is being administered under the skin of a living subject.

FIG. 5 shows delivery implant 40, loaded with active agent 44, being administered under the skin 50 of a patient. Plunger 30 is forced into the cannulation 25 of needle 22 by application of a force on flange 38. Delivery implant 40, loaded with active agent 44, is forced out of the distal end of needle 22 by plunger 30. Delivery implant 40 is fully administered when the distal end of plunger 30 reaches the distal end of needle 22.

While it is possible to begin displacement of the active agent 44 into the delivery implant 40 prior to the needle 22 penetrating the skin 50, it is preferred that the needle 22 of implant insertion device 10 penetrates the skin 50 of the patient prior to the loading of active agent 44 into delivery implant 40. That is, prior to plunger 30 being forced into the cannulation 21 of barrel 20 by application of a force on flange 38.

In this manner, the implant insertion device 10 of this invention allows for a simple, one-step process for loading the delivery implant 40 with active agent 44 at the time the implant is being inserted into the patient. After inserting the needle 22 into the patent, the health professional administering the delivery implant forces the plunger 30 into the barrel 20. In one step, the active agent 44 is loaded into the delivery implant 40, and the implant 40 is administered to the patient. By loading the delivery implant 40 at the time of insertion, issues of processing and shelf-life of preloaded delivery implants are avoided.

In accordance with one method of loading the implant insertion device 10 prior to use, the hub 24 is first attached to the barrel 20 by means described above. The plunger 30 is inserted into the cannulation 21 of the barrel 20 until the distal end of the plunger 30 reaches the distal end of the barrel 20. The cannulation 21 of the barrel 20 is filled with the appropriate amount of active agent 44 by moving the plunger 30 proximally, which, in the case of a flowable active agent 44, such as a liquid or gel, will draw the active agent 44 into the cannulation 21 of barrel 20 as the plunger 30 retreats in a proximal direction.

In accordance with another method, the plunger 30 is partially inserted into the cannulation 21 of the barrel 20, and the active agent 44 metered into the cannulation 21 through the distal end, of the barrel 20, e.g., through the hub cannula 29. If the active agent 44 is flowable, then the hub cannula 29 may be plugged with rubber or resin to eliminate evaporation or leakage during storage. Prior to injection of the implant, the hub cannula 29 plug 33 (shown diagrammatically in FIG. 4 by dotted lines) may be removed or pierced. The hub cannula 29 plug or seal 33 may be in the form of a rupturable membrane that ruptures under the pressure exerted on the plunger 30 by the user of the device 10.

In separate process steps, the needle 22 portion of the implant insertion device 10 may be prepared for assembly to the hub 24 as follows. The needle 22 with press fit collar 34 is passed through the bore in the cap 28 and the gasket 32 is placed on the needle 22 abutting the collar 34. The delivery implant 40 is then inserted into the cannulation 25 of the needle 22, thus completing preparation for the assembly of needle portion 22 to the hub 24.

If the active agent 44 is sealed in cannulation 21 of barrel 20 by a plug 33 or membrane occluding hub cannulation 29,, then the barrel 20 and needle 22 of the implant insertion device 10 may be assembled prior to packaging and sterilization. Alternatively, the active agent 44 may be stored separately from the device 10 and introduced into the device 10, i.e., by the methods outlined above, just prior to injection of the delivery implant 40.

If different means of sterilization are required for the delivery implant 40, the device 10 and the active agent, then it is preferred that each of these components be packaged and sterilized separately. In this manner, degradation of the active agent 44 due to exposure to, e.g., radiation used to sterilize the device 10, can be avoided. The separate portions of the device may then be assembled as described above at the time of use by the medical professional.

As mentioned earlier, if a prior art delivery implant is made from a biodegradable polymer, there are inherent problems presented by combining the biodegradable polymer with a medicament containing an active agent. These include having to use complex processing techniques so as not to harm the active agent, being concerned with the shelf-life of the polymer/active agent composition after processing and compatibility issues between the active agent and the polymer such as if the medicament is aqueous based, and the polymer degrades when exposed to water. In accordance with the present invention, by loading the delivery implant at the time of insertion, issues of undesirable processing and shelf-life reactions are avoided.

A variety of biodegradable polymers can be used to make the delivery implant 40 of the present invention. Examples of suitable biocompatible, biodegradable polymers include polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-,L- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, $\gamma$-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof.

The active agent 44 used in the implant insertion device 10 of the present invention may be of a pharmacological and/or cellular nature. The variety of different pharmacological agents that can be used in conjunction with the present invention is vast. In general, pharmacological agents which may be administered via this invention include, without limitation: antiinfectives such as antibiotics and antiviral agents; chemotherapeutic agents (i.e. anticancer agents); anti-rejection agents; analgesics and analgesic combinations; anti-inflammatory agents; hormones such as steroids; antigens, including but not limited to cytokines, attachment factors, genes, peptides, proteins, nucleotides, carbohydrates or even cells or cell fragments; growth factors, including bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-$\beta$I-III), vascular endothelial growth factor (VEGF); and other naturally derived or genetically engineered proteins, polysaccharides, glycoproteins, or lipoproteins.

The pharmacological agent may be present as a liquid, or formulated in a solution, suspension, or gel containing the component(s), or any other appropriate physical form. Typically, but optionally, additives, such as diluents, carriers, excipients, stabilizers or the like may be included in the formulation.

The amount of pharmacological agent will depend on the particular medical condition being treated, and will vary depending on the release profile desired and the amount of drug employed. Prolonged delivery (over, say 1 to 5,000 hours, preferably 2 to 800 hours) of effective amounts (say, 0.0001 mg/kg/hour to 10 mg/kg/hour) of the agent are desired. This dosage form can be administered as is necessary depending on the subject being treated, the severity of the affliction, the judgment of the prescribing physician, and the like. Following this or similar procedures, those skilled in the art will be able to prepare a variety of formulations.

Active agents of the present invention may also be cellular by nature. Cells which can be loaded into the delivery implant of the current invention include, but are not limited to, bone marrow cells, stromal cells, stem cells, embryonic stem cells, chondrocytes, osteoblasts, osteocytes, osteoclasts, fibroblasts, pluripotent cells, chondrocyte progenitors, endothelial cells, macrophages, leukocytes, adipocytes, monocytes, plasma cells, mast cells, umbilical cord cells, mesenchymal stem cells, epithelial cells, myoblasts, islet of langerhom, and precursor cells derived from adipose tissue. The cells can be loaded into the delivery implant of the present invention for a short period of time, e.g. less than one day, just prior to implantation, or cultured for longer a period, e.g. greater than one day, to allow for cell proliferation and matrix synthesis within the delivery implant prior to implantation.

Cells typically have at their surface, receptor molecules which are responsive to a cognate ligand (e.g., a stimulator). A stimulator is a ligand which when in contact with its cognate receptor induce the cell possessing the receptor to produce a specific biological action. For example, in response to a stimulator (or ligand) a cell may produce significant levels of secondary messengers, like $Ca^{+2}$, which then will have subsequent effects upon cellular processes such as the phosphorylation of proteins, such as (keeping with our example) protein kinase C. In some instances, once a cell is stimulated with the proper stimulator, the cell secretes a cellular messenger usually in the form of a protein (including glycoproteins, proteoglycans, and lipoproteins). This cellular messenger can be an antibody (e.g., secreted from plasma cells), a hormone, (e.g., a paracrine, autocrine, or exocrine hormone), or a cytokine.

The following examples are illustrative of the principles and practice of this invention. Numerous additional embodiments within the scope and spirit of the invention will become apparent to those skilled in the art.

EXAMPLE 1
(A Prototypical Implant Insertion Device 10)

A 10 µl glass syringe (part# 701RN, Hamilton Company, Reno, Nev.) with a removable needle was purchased. A thin-walled, 18° pointed, 20 gauge needle, 1.125-inches long was also purchased (Popper and Sons, Inc., New Hyde Park, N.Y.). Collars and gaskets were machined using 316 stainless steel and poly(tetrafluoro ethylene) (sold under the tradename TEFLON by E.I. duPont, Wilmington, Del.), respectively. The dimensions of both were 0.105-inch height×0.125-inch diameter). Through the center of each collar and gasket was drilled a 0.0355-inch diameter hole. The collar was press-fit onto the 20 gauge needle, with the distal end of the collar 0.2-inch from the proximal end of the needle. The TEFLON gasket was then press-fit onto the proximal end of the needle and seated snugly against the proximal end of the collar. A 0.042-inch diameter hole was drilled in the center of the threaded, knurled cap. The distal end of the needle was placed first through the proximal end of the hole in the cap and pulled through until the distal end of the press-fit collar was seated on the inside of the cap. A 316 stainless steel plunger 4.188 inches in length was centerless ground to a diameter of 0.0185±0.0002-inch. To one end of this plunger was press-fit a stainless steel flange for the thumb.

EXAMPLE 2
(A Prototypical Delivery Implant)

Tubing was melt extruded from an elastomeric copolymer of ε-caprolactone (CAP) and glycolide (GLY) having a mole ratio of ε-caprolactone to glycolide of about 35/65 (35/65 CAP/GLY, Ethicon, Inc., Somerville, N.J.). The inherent viscosity (IV) of the 35/65 CAP/GLY was about 1.3 deciliters per gram (dL/g), as measured in a 0.1 g/dL solution of hexafluoroisopropanol (HFIP) at 25° C. The tubing had an outer diameter of approximately 0.0256 inches and an inner diameter of approximately 0.0177 inches. Pieces of this tubing 1-inch in length were cut with a razor blade. The inside of each piece of tubing was filled with about 2 mg of fibers composed of 90/10 copolymers of poly(glycolic acid) with poly(lactic acid) (PGA/PLA), sold under the tradename VICRYL (Ethicon, Inc., Somerville, N.J.). As this example teaches, the present invention comprehends a delivery implant 40, the hollow 27 of which is partially filled with filler 31 (shown diagrammatically in FIG. 4) such as fillers, fibers or a foam into which the active agent 44 infiltrates. Such fillers can be advantageous with respect to holding and metering out liquid active agents 44 to assist in controlled release of the active agent 44.

EXAMPLE 3
(Illustrating the Operation of the Implant Insertion Device 10)

A solution was made containing ~0.1% Nigrosin dye (Aldrich Chemicals, Milwaukee, Wis., part # 19,828-5) in deionized water. Approximately 2.5 µl of this die solution was drawn into the syringe barrel through a 30 gauge needle. The 30 gauge needle was then removed from the syringe barrel. A fiber-filled 1-inch long piece of tubing from Example 2 was placed into the proximal end of a 20 gauge needle from Example 1. The needle assembly was attached to the syringe barrel. The plunger was depressed until the fiber filled tube was expelled out the end of the needle. Upon inspection the tube was filled with the dyed liquid.

We claim:

1. A system for implanting medicinal implants into the body of a living creature, comprising:
   an injector body with a first lumen therein;
   a plunger slideable within said first lumen between a retracted position and a deployed position;
   a needle having a second lumen therein, said needle coupled to said injector body with said second lumen communicating with said first lumen; and
   an injectable implant having a hollow interior and positionable within at least one of said first lumen and said second lumen, said hollow interior communicating with said first lumen; and
   a medicament, storable at least partially within said first lumen separate from said injectable implant to prevent interaction therebetween when said plunger is in said retracted position, said hollow interior of said injectable implant receiving at least a portion of said medicament when said plunger is moved from said retracted position to said deployed position, said plunger pushing said injectable implant through said second lumen and out of said needle when said plunger assumes said deployed position.

2. The system of claim 1, wherein said implant is biodegradable and provides a selected rate of release of said medicament into the body of the creature.

3. The system of claim 2, wherein said injectable implant is formed from a material selected from the group consisting of biodegradable polymers, biopolymers, bioabsorbable starches and blends thereof.

4. The system of claim 1, wherein a phase of said medicament is selected from the group consisting of solid, liquid, gel, suspensions and paste.

5. The system of claim 4, wherein said medicament has an active agent component selected from the group consisting of antibiotics, antiviral agents, anticancer agents, anti-rejection agents, analgesics, anti-inflammatory agents, hormones, antigens, cyotkines, attachment factors, genes, peptides, proteins, nucleotides, carbohydrates, cells, cell fragments, growth factors, polysaccharides, glycoproteins and lipoproteins.

6. The system of claim 1, wherein said injectable implant has an input opening to admit said medicament and a vent to discharge gas displaced by said medicament.

7. The system of claim 6, wherein said injectable implant is substantially tubular in shape.

8. The system of claim 6, wherein said injectable implant has cross-sectional dimensions approximating the cross-sectional dimensions of said first lumen.

9. The system of claim 1, further including a filler disposed within said hollow interior of said injectable implant, said medicament diffusable into said filler.

10. The system of claim 9, wherein said filler is a biodegradable fiber.

11. The system of claim 1, wherein said injectable implant has a friction fit relationship relative to at least one of said first lumen and said second lumen.

12. The system of claim 1, further including a seal disposed in a distal end of said first lumen, said seal retaining said medicament within said first lumen when said plunger is in said retracted position.

13. The system of claim 12, wherein said seal is a removable plug.

14. The system of claim 12, wherein said seal is a rupturable membrane.

15. The system of claim 1, wherein said needle is removably coupled to said injector body.

16. The system of claim 15, wherein said injector body includes an elongated cylindrical barrel with a threaded nipple at a distal end thereof, said needle having a peripheral collar disposed proximate a first end thereof and further comprising a needle retention cap having a threaded bore terminating in a bridging cap member with a needle bore therein for accommodating said needle therethrough, said threaded bore being threadedly receivable on said threaded nipple, said bridging cap member abutting said peripheral collar for urging said needle toward said threaded nipple when said needle retention cap is threadedly received thereon.

17. The system of claim 16, wherein said nipple has a needle aperture therethrough communicating with said first lumen, said needle aperture slideably receiving said first end of said needle, and further comprising a gasket slideable over said needle proximate said first end, said gasket being captured between said collar and said nipple when said needle retention cap is received on said nipple.

18. The system of claim 15 wherein said needle is removably coupled to said injection body by a Leur-type connector.

19. A method for introducing a medicament into the body of a living creature, comprising the steps of:

(A) providing an injector having a first lumen therein, a plunger slideable within the first lumen between a retracted position and a deployed position and a needle with a second lumen disposed at one end of the injector for penetrating the body of the creature;

(B) providing an injectable implant with a hollow interior;

(C) charging the first lumen with a medicament;

(D) inserting the injectable implant into the second lumen;

(E) maintaining the injectable implant and the medicament separate to prevent chemical interaction therebetween after completion of said steps of charging and inserting;

(F) penetrating the body of the creature with the needle; and (G) moving the plunger from the retracted position to the deployed position, the plunger moving the medicament into the hollow interior of the injectable implant as it moves from the retracted position towards an intermediate position contacting the injectable implant and pushing the injectable implant out of the needle and into the body of the creature as the plunger moves to the deployed position.

20. The method of claim 19, further comprising the step of assembling the needle to the injector just prior to moving the plunger in said step G.

21. The method of claim 20, further comprising the step of sterilizing the injector and the injectable implant separately from the medicament and prior to moving the medicament into the hollow interior of the injectable implant in said step G.

22. The method of claim 19, wherein the medicament has approximately the same volume as said hollow interior.

23. The method of claim 19, wherein the medicament includes living cells and further comprising the step of waiting to move the plunger after the plunger has reached the intermediate position in order to allow the cells to interact with the injectable implant prior to penetrating the body with the needle and prior to injecting the injectable implant into the body of the creature.

24. The method of claim 19, further comprising the steps of (E2) packaging the injector after said steps of (C) charging and (D) inserting and during said step (E) of maintaining and subsequently (E3) unpacking the injector while still performing said step of maintaining and prior to said step (F) of penetrating.

25. The method of claim 19, further comprising the steps (H) of retaining medicament in the hollow interior of the injectable implant after said step (G) of pushing and (I) releasing the medicament from the hollow interior into the body of the creature over a period of from 2 to 800 hours.

26. A method for introducing a medicament into the body of a living creature, comprising the steps of:

(A) providing an injector having a first lumen therein, a plunger slideable within the first lumen between a retracted position and a deployed position and a needle with a second lumen disposed at one end of the injector for penetrating the body of the creature;

(B) providing an injectable implant with a hollow interior;

(C) charging the first lumen with a medicament;

(D) sealing the medicament in the first lumen;

(E) inserting the injectable implant into the second lumen;

(F) penetrating the body of the creature with the needle;

(G) overcoming the sealing of the medicament in the first lumen; and (H) moving the plunger from the retracted position to the deployed position, the plunger moving the medicament into the hollow interior of the injectable implant as it moves from the retracted position towards an intermediate position contacting the injectable implant and pushing the injectable implant out of the needle and into the body of the creature as the plunger moves to the deployed position.

* * * * *